(12) United States Patent
Chen

(10) Patent No.: US 7,300,676 B2
(45) Date of Patent: Nov. 27, 2007

(54) HERBAL COMPOSITION FOR TREATMENT OF DIGESTIVE AND URINARY DISORDERS

(76) Inventor: Jiafang Chen, 169 River Meadow Ct., Laurenceville, GA (US) 30043

( * ) Notice: Subject to any disclaimer, the term of this patent is extended or adjusted under 35 U.S.C. 154(b) by 202 days.

(21) Appl. No.: 11/082,987

(22) Filed: Mar. 18, 2005

(65) Prior Publication Data

US 2005/0163870 A1    Jul. 28, 2005

Related U.S. Application Data

(62) Division of application No. 10/307,651, filed on Dec. 2, 2002, now abandoned.

(51) Int. Cl.
*A61K 36/00* (2006.01)
(52) U.S. Cl. .................................... 424/725
(58) Field of Classification Search ............... None
See application file for complete search history.

(56) References Cited

U.S. PATENT DOCUMENTS 5,324,516 A * 6/1994 Pek et al. ................... 424/727
5,595,756 A * 1/1997 Bally et al. ................. 424/450
5,874,084 A * 2/1999 Yng-Wong ................. 424/740

OTHER PUBLICATIONS

Gura, T. Systems for Identifying New Drugs are Often Faulty; Science, vol. 278, Nov. 1997, pp. 1041-1042.*

* cited by examiner

*Primary Examiner*—Patricia Leith
(74) *Attorney, Agent, or Firm*—MH2 Technology Law Group, LLP

(57) ABSTRACT

The present invention includes compositions and methods of treating and preventing prostate and urinary problems in human males. Additionally, methods of digestive system improvement, blood circulation system improvement, liver and kidney system improvement and urinary system improvement are included.

6 Claims, No Drawings

HERBAL COMPOSITION FOR TREATMENT OF DIGESTIVE AND URINARY DISORDERS

FIELD OF THE INVENTION

This is a division of application Ser. No. 10/307,651, filed Dec. 2, 2002, now abandoned which is incorporated herein by reference in its entirety.

The present invention relates to improvements in animal health, especially the health of humans, particularly male humans. The medical systems of an animal, especially the digestive system, blood circulation system, urinary system, and liver and kidney system, and overall health may be improved by the present invention.

BACKGROUND OF THE INVENTION

The prostate is a male reproductive gland, which is located below the bladder and adjacent to the rectum. A normal sized prostate gland is about the size of a walnut and encircles at least part of the urethra (which is the tube used to empty the bladder of urine). Fluid is produced by the prostate gland which then becomes part of the semen.

With age, the prostate gland may enlarge and ultimately block the urethra or bladder. This blockage can cause pain and difficulty in urination and sexual activity may be effected. While not malignant, this condition is called benign hyperplasia (hereinafter "BPH"), and may need to be corrected with surgery. Additionally, many of the symptoms of BPH are also symptoms of prostate cancer.

Prostate cancer is a disease manifested in malignant (cancerous) cells in the prostate tissues. This disease is found mainly in older men. Symptoms include, but are not limited to, weak flow of urine, interrupted flow of urine, frequent urination (especially at night), difficulty urinating, pain or burning during urination, blood in urine, blood in semen, pain in the back, hips or pelvis, and painful ejaculation.

There are several tests for detecting prostate cancer including but not limited to digital rectal examination, PSA test (a lab test that measures the prostate-specific antigen (hereinafter "PSA") levels in a blood sample), transrectal ultrasound, and biopsy.

PSA is a substance produced by the prostate gland and is often found in increased amount in the blood of prostate cancer victims. Other reasons for elevated PSA levels include infection of the prostate, inflammation of the prostate, or BPH.

PSA levels of less than about 2 ng/ml are associated with a very low risk of cancer. PSA levels from about 4 to about 10 ng/ml are borderline. It is estimated that about 20% to about 30% of men with PSA levels in this range have prostate cancer. About 40% to about 60% of men with PSA levels greater than about 10 ng/ml, are estimated to have prostate cancer. Healthcare professionals usually follow up the PSA test with transrectal ultrasounds and/or biopsies.

Traditional Chinese Medicine (hereinafter "TCM") does not usually address prostate cancer. See, e.g., Department of TCM Formulas, Beijing TCM University, ed. 195; Tang Tou Ge Jue Bai Hua Jie (Modern Chinese Version of Ancient TCM Formulas), p. 109-121, and 166-176 (Beijing, PRC); People's Hygienic Press; Shanghai TCM University ed. 1998; Fang Ji Xue (TCM Formulas), p. 98-107 (Hong Kong); Commercial Press; Lu, Henry C., 195 Chinese Natural Cure, p. 245-271 (Toronto); Black Dog & Leventhal Publishers; and Wang, Jinhong ed., Effective TCM Formulas for Neurological and Endocrinological Diseases, p. 237-240, and 280-295 (Jiangsu, PRC).

Other forms of medicine, other than TCM, utilize PSA levels to gauge levels of cancerous activity. TCM is only now beginning to examine liver and kidney system (including, but not limited to kidney, liver and gallbladder) and urinary system (including but not limited to urinary and reproductive organs) problems. These problems may be assessed through, but are not limited to, checking acupuncture points, pulse readings and physical examination of the tongue. Additionally, physical symptoms include but are not limited to swollen prostate and pain or burning during urination.

Conventional (non-TCM) prostate cancer treatments have undesirable side effects. These include but are not limited to incontinence and erectile dysfunction. Combining these side effects with the uncertain impact of treatment on the chance for survival, heightens the need for other treatment and prevention methods.

Prostate and urinary related problems such as, but not limited to, swollen or enlarged prostate, high PSA, pain and/or burning sensations during urination and prostate cancer may be prevented and/or treated by the present invention.

SUMMARY OF THE INVENTION

The present invention may be used to treat and/or prevent prostate and urinary problems in animals, preferably human, most preferably human males, including but not limited to prostate cancer, especially the early stages of prostate cancer.

A composition comprising one or more digestive system improvement herbs, one or more blood circulation improvement (including but not limited to maintaining about normal blood temperature, or maintaining about normal and about constant blood flow) herbs, one or more urinary system improvement herbs, one or more liver and kidney system improvement herbs, or combinations thereof is one embodiment of the invention. Herbs are defined to include, but are not limited to, herbs, herbal extracts, any part of an herb, chemicals, chemical extracts, medicine and medicinal substances.

Additionally, an embodiment of the invention is a method of preventing and/or treating prostate problems (including but not limited to, enlarged prostate, prostate cancer, and elevated (benign, precancerous or malignant) levels of PSA, pain during urination, and burning during urination) by administering a composition comprising one or more digestive system improvement herbs, one or more blood circulation improvement herbs, one or more urinary system improvement herbs, one or more liver and kidney system improvement herbs, or combinations thereof.

The digestive system performs the functions of digesting foods, absorbing nutrients, delivering nutrients and fluid to the rest of the body, and helps to make blood. Without being limited or held to the mechanisms, it is believed that the normal functioning of digestive system provides a foundation for a healthy body and a strong immune system.

Another embodiment of the invention is a method of improving performance of the digestive system of an animal by administering a composition comprising astragali seu hedysari radix, codonopsis pilosulee radix, atractylodes rhizoma, poria cocos, raphani semen, xingiberis siccatun rhizoma, atractylodis lanceae rhizoma, amomi fructus, agastache rugosa herba, artemisiae capillaris herba, coicis semen, dianthi herba, evodias fructus, alpiniae officinarum rhizoma, foeniculi fructus, saussureae radix, cyperi rhizoma, crataegi fructus, massa medicata fermentata, endothelium corheum gigeriae galli, hordei germinatus fructus, oryzae fructus, dioscorea batais rhizoma, dolichoris semen, zizyphi fructus, glycyrrhizae radix, polygonati rhizoma, hominis placenta, reticulatae pericarpium citri or combinations thereof. Improvement of the digestive system may increase the efficiency of the immune system of the animal.

Another embodiment of the invention is a method of improving blood circulation of an animal by administering a composition comprising rehmanniae radix, gardeniae fructus, moutan radicis cortex, glehniae radix, adenophorae radix, asparigi radix, ophiopogonis radix, dendrobii herba, ecliptae herba, carapax et plastrum testudinis, plastrum testudinis, agrimoniae herba, callicar pa pedunculata, cephalanoploris herba, cacumen biota, sophorae flos, sanguisorbae radix, rubiae radix, typhae pollen, loti rhizomatis nodus, notoginseng radix, tribuli fructus, haematitum, bupleuri radix, lycii radicis cortex, paeoniae rubra radix, lithospermi radix, baphicanthis folium, scrophulariae radix, imperatae rhizoma, prunellae spica, salviae miltiorrhziae radix, cnidii rhizoma (ligustici rhizoma), persicae semen, carthami flos, vaccariae semen, sparganii rhizoma, zedoariae rhizoma, gleditsiae spina, paederiae caulis, centranthera cochinchinensis semen, or combinations thereof.

Another embodiment of the invention is a method of maintaining blood temperature of an animal by administering a composition comprising rehmanniae radix, gardeniae fructus, moutan radicis cortex, glehniae radix, adenophorae radix, asparigi radix, ophiopogonis radix, dendrobii herba, ecliptae herba, carapax et plastrum testudinis, plastrum testudinis, agrimoniae herba, callicar pa pedunculata, cephalanoploris herba, cacumen biota, sophorae flos, sanguisorbae radix, rubiae radix, typhae pollen, loti rhizomatis nodus, notoginseng radix, tribuli fructus, haematitum, bupleuri radix, lycii radicis cortex, paeoniae rubra radix, lithospermi radix, baphicanthis folium, scrophulariae radix, imperatae rhizoma, prunellae spica, salviae miltiorrhziae radix, cnidii rhizoma (ligustici rhizoma), persicae semen, carthami flos, vaccariae semen, sparganii rhizoma, zedoariae rhizoma, gleditsiae spina, paederiae caulis, centranthera cochinchinensis semen, or combinations thereof.

The urinary system includes the bladder and urinary track, and in males, the prostate gland. Another embodiment of the invention is a method of improving the function of the urinary system of an animal by administering a composition comprising one or more of the group consisting of gelchoma herba, dioscoreae hypoglauca rhizoma, lygodii spora, ostreae testa, taraxaci herba, lopatheri herba, gypsum fibrosum, lonicerae flos, frosythiae fructus, violae herba, houttuyniae herba, thlaspi herba, smilacis glabrae rhizoma, portulacae herba, phaseolus radiatus, phizoma paridis, hedyotis diffasae herba, phellodendri cortex, gentianae radix, sophorae radix, scutellariae radix, polyprous, alismatis rhizoma, plantaginis herba, plantaginis semen, tetrapanax papyriferus, phaseolus calcaratus roxb, mydis stigma, gryllulus chinensis weber, kochiae fructus, polygoni avicularis herba, pyrrosiae folium, talcum and kaolinum, succinum, lumbricus, manitis squama, pinellia rhizoma, pumex, concha arcae, cyclina senensis, or combinations thereof.

The liver and kidney system performs the functions of blood storage and blood purification, blood supply regulation, partially regulates blood circulation, regulates the functions of the urinary system, may promote body growth, consolidates the quality of bone and partially regulates the discharge of body fluid.

Another embodiment of the invention is a method of improving liver and kidney system of an animal by administering a composition comprising one or more of the group consisting of achyranthis radix, morindae radix, rehmanniae radix, schizandrae fructus, comi fructus, euryalis semen, mantidis otheca, loranthi ramulus, plastrum testudinis, ligustri lucidi fructus, lycii fructus, euphora longan, mori fructus, asini gelatinum, paeoniae alba radix, angelicae radix, polygoni multiflori radix, eucommiae cortex, cibotii rhizoma, dipsaci radix, cnidii monnieri fructus, cordyceps senesis, gekko gecko, cuscutae semen, cistanchis herba, alpinia oxyphyllae fructus, epimedii herba, cervus nippon, *C. elaphus*, cervi degelatinatum cornu, uncariae ramulus cum uncis, immaturi pericarpium citri, sarcodactyli fructus citri, litchi chinensis semen, aurantii semen, cinnamomi cortex, homalomenae rhizoma, acanthopanacis cortex, luffae fasciculus vascularis, or combinations thereof.

DETAILED DESCRIPTION OF SEVERAL EMBODIMENTS

Unlike conventional treatments and preventative measures for prostate and urinary problems, without being limited or held to the mechanism, the present invention utilizes herbs to improve the function of the digestive system. This improvement of the digestive system may enhance the immune system and bolster the natural defense of the animal body, preferably the human body, more preferably the male human body. Without being limited or held to mechanisms, this natural defense appears to be crucial in terms of treating many disorders and diseases, including but not limited to prostate cancer, prostate problems, urinary problems, immune system problems, cardiovascular problems, pulmonary problems, reproductive problems, neurological problems, endocrine and metabolic problems, gastrointestinal problems, hepatic and biliary problems, musculaskeleta and connective tissue problems, dermatological problems, and hematological and oncological problems.

The immune system includes the natural defense system of the animal, which wards off disease, infections, viruses, and other illnesses and disorders.

Additionally, without being limited or held to the mechanism, the present invention improves blood circulation, which may help keep blood temperature about normal. Stable, normal blood temperature for an animal may help reduce infection of the prostate and improve the urination function (including but not limited to by regular frequency of urination, eliminating pain and burning during urination, and normalizing flow of urine). Stable, normal blood temperature for an animal may help reduce infection of various organs, including but not limited to the liver, kidneys, and immune system.

The present invention has many embodiments, including but not limited to, mixing the herbs and boiling the mixture to yield a tea, pulverizing the herbs to a powder (preferably a fine powder) and mixing it with water for ingestion, abstracting herbal extracts using chemical solvents which are conventionally known, and preferably pulverizing herbs, encapsulating them and ingesting the capsules orally.

The dosage for an animal may vary according to its health and condition. An average dose is about 20 to about 90 grams, preferably about 20 to about 23 grams or about 80 to about 90 grams, most preferably about 40 to about 45 grams of the mixture. This dose is preferably taken about one to about three times a day, preferably about two to about three times a day. The dose is taken for preferably about 180 to about 730 days.

The digestive system improvement herbs include but are not limited to the following:

| Chinese Pin Yin (Chinese Name) | Latin |
|---|---|
| Huang Qi (Sheng) | Astragali seu Hedysari Radix |
| Dang Shen | Codonopsis Pilosulae Radix |
| Bai Zhu | Atractylodes Rhizoma |
| Fu Ling | Poria Cocos |
| Lai Fu Zi | Raphani Semen |
| Gan Jiang | Zingiberis Siccatun Rhizoma |
| Cang Zhu | Atractylodis Lanceae Rhizoma |
| Sha Ren | Amomi Fructus |
| Huo Xiang | Agastache Rugosa Herba |
| Yin Chen | Artemisiae Capillaris Herba |
| Yi Ren | Coicis Semen |
| Qu Mai | Dianthi Herba |
| Wu Zhu Yu | Evodiae Fructus |
| Gao Liang Jiang | Alpiniae Officinarum Rhizoma |
| Xiao Hui Xiang | Foeniculi Fructus |
| Mu Xiang | Saussureae Radix |
| Xiang Fu | Cyperi Rhizoma |
| Shan Zha | Crataegi Fructus |
| Shen Qu | Massa Medicata Fermentata |
| Ji Nei Jin | Endothelium Corneum Gigeriae Galli |
| Mai Ya | Hordei Germinatus Fructus |
| Gu Ya | Oryzae Fructus |
| Shan Yao (Huai) | Dioscorea Batatis Rhizoma |
| Bai Bian Dou | Dolichoris Semen |
| Da Zao | Zizyphi Fructus |
| Gan Cao | Glycyrrhizae Radix |
| Ren Shen | Ginseng Radix |
| Huang Jing | Polygonati Rhizoma |
| Zi He Che | Hominis Placenta |
| Chen Pi | Reticulatae Pericarpium Citri |

The blood circulation improvement herbs include but are not limited to the following:

| Chinese Pin Yin | Latin |
|---|---|
| Sheng Di Huang | Rehmanniae Radix |
| Zhi Zi | Gardeniae Fructus |
| Mu Dan Pi | Moutan Radicis Cortex |
| Sha Shen (Bei) | Glebniae Radix |
| Sha Shen (Nan) | Adenophorae Radix |
| Tian Dong | Asparigi Radix |
| Mai Dong | Ophiopogonis Radix |
| Shi Hu | Dendrobii Herba |
| Han Lian Cao | Ecliptae Herba |
| Gui Ban (Zhi) | Carapax et Plastrum Testudinis |
| Bie Jia (Zhi) | Plastrum Testudinis |
| Xian He Cao | Agrimoniae Herba |
| Zi Zhu Cao | Callicar pa Pedunculata |
| Xiao Ji | Cephalanoploris Herba |
| Ce Bai Ye | Cacumen Biota |
| Huai Hua | Sophorae Flos |
| Di Yu | Sanguisorbae Radix |
| Qian Cao | Rubiae Radix |
| Pu Huang | Typhae Pollen |
| Ou Jie | Loti Rhizomatis Nodus |
| San Qi | Notoginseng Radix |
| Bai Ji Li | Tribuli Fructus |
| Dai Zhe Shi | Haematitum |
| Chai Hu | Bupleuri Radix |
| Di Gu Pi | Lycii Radicis Cortex |
| Chi Shao | Paeoniae Rubra Radix |
| Zi Cao | Lithospermi Radix |
| Da Qing Ye | Baphicacanthis Folium |
| Xuan Shen | Scrophulariae Radix |
| Mao Gen | Imperatae Rhizoma |

| Chinese Pin Yin | Latin |
|---|---|
| Xia Ku Cao | Prunellae Spica |
| Dan Shen | Salviae Miltiorrhziae Radix |
| Chuan Xiong | Cnidii Rhizoma (Ligustici Rhizoma) |
| Tao Ren | Persicae Semen |
| Hong Hua | Carthami Flos |
| Wang Bu Liu Xing | Vaccariae Semen |
| San Leng | Sparganii Rhizoma |
| E Zhu | Zedoariae Rhizoma |
| Zao Jiao Ci | Gleditsiae Spina |
| Ji Xie Teng | Paederiae Caulis |
| Hu Ma Ren | Centranthera Cochinchinensis Semen |

The urinary system improvement herbs include but are not limited to the following:

| Chinese Pin Yin | Latin |
|---|---|
| Jin Qian Cao | Glechoma Herba |
| Bei Xie | Dioscoreae Hypoglauca Rhizoma |
| Hai Jin Sha | Lygodii Spora |
| Mu Li (Duan) | Ostreae Testa |
| Pu Gong Ying | Taraxaci Herba |
| Zhu Ye | Lopatheri Herba |
| Shi Gao | Gypsum Fibrosum |
| Jin Yin Hua | Lonicerae Flos |
| Lian Qiao | Forsythiae Fructus |
| Zi Hua Di Ding | Violae Herba |
| Yu Xing Cao | Houttuyniae Herba |
| Bai Jiang Cao | Thlaspi Herba |
| Tu Fu Ling | Smilacis Glabrae Rhizoma |
| Ma Chi Xian | Portulacae Herba |
| Lu Dou | Phaseolus Radiatus |
| Qi Ye Yi Zhi Hua | Phizoma Paridis |
| Bai Hua She She cao | Hedyotis Diffasae Herba |
| Huang Bai | Phellodendri Cortex |
| Long Dan Cao | Gentianae Radix |
| Ku Shen | Sophorae Radix |
| Huang On | Scutellariae Radix |
| Zhu Ling | Polyporus |
| Ze Xie | Alismatis Rhizoma |
| Che Qian Cao | Plantaginis Herba |
| Che Qian Zi | Plantaginis Semen |
| Tong Cao | Tetrapanax Papyriferus |
| Chi Xiao Dou | Phaseolus Calcaratus Roxb |
| Yu Mi Xu | Maydis Stigma |
| Xi Shuai | Gryllulus Chinensis Weber |
| Di Fu Zi | Kochiae Fructus |
| Bian Xu | Polygoni Avicularis Herba |
| Shi Wei | Pyrrosiae Folium |
| Hua Shi | Talcum and Kaolinum |
| Hu Po | Succinum |
| Di Long | Lumbricus |
| Chuan Shan Jia | Manitis Squama |
| Ban Xia (Fa) | Pinellia Rhizoma |
| Nan Xing (Zhi) | Arisaematis Rhizoma |
| Hai Fu Shi | Pumex |
| Wa Leng Zi (Duan) | Concha Arcae |
| Hai Ge Ke | Cyclina Senensis |

The liver and kidney system improvement herbs include but are not limited to the following:

| Chinese Pin Yin | Latin |
|---|---|
| Niu Xi (Huai) | Achyranthis Radix |
| Ba Ji Tian | Morindae Radix |
| Shou Di Huang | Rehmanniae Radix |
| Wu Wei Zi | Schizandrae Fructus |
| Shan Zhu Yu | Corni Fructus |

-continued

| Chinese Pin Yin | Latin |
|---|---|
| Qian Shi | Euryalis Semen |
| Sang Piao Xiao | Mantidis Otheca |
| Sang Ji Sheng | Loranthi Ramulus |
| Bie Jia | Plastrum Testudinis |
| Nu Zhen Zi | Ligustri Lucidi Fructus |
| Gou Qi Zi | Lycii Fructus |
| Gui Yuan | Euphoria Longan |
| Sang Shen Zi | Mori Fructus |
| E Jiao | Asini Gelatinum |
| Bai Shao | Paeoniae Alba Radix |
| Dang Gui | Angelicae Radix |
| He Shou Wu | Polygoni Multiflori Radix |
| Du Zhong | Eucommiae Cortex |
| Jin Gou Ji | Cibotii Rhizoma |
| Xu Duan | Dipsaci Radix |
| She Chuang Zi | Cnidii Monnieri Fructus |
| Chong Cao | Cordyceps Senensis |
| Ge Jie | Gekko Gecko |
| Tu Si Zi | Cuscutae Semen |
| Rou Cong Rong | Cistanchis Herba |
| Yi Zhi Ren | Alpinia Oxyphyllae Fructus |
| Yin Yang Huo | Epimedii Herba |
| Lu Rong | Cervus Nippon, C. Elaphus |
| Lu Jiao Shuang | Cervi Degelatinatum Cornu |
| Gou Teng | Uncariae Ramulus Cum Uncis |
| Qing Pi | Immaturi Pericarpium Citri |
| Fuo Shou | Sarcodactyli Fructus Citri |
| Li Zhi He | Litchi Chinensis Semen |
| Ju He | Aurantii Semen |
| Rou Gui | Cinnamomi Cortex |
| Qian Nian Jian | Homalomenae Rhizoma |
| Wu Jia Pi | Acanthopanacis Cortex |
| Si Gua Luo | Luffae Fasciculus Vascularis |

Further, the effect of administering the composition embodied as described in this specification may be enhanced by additional measures. In one embodiment, the patient abstains from eating almost all cold drinks and all cold foods (i.e. drinks and food below room temperature) during the administration period. The administration period is during the administration of the composition. Preferably, the patient alters his/her lifestyle to consume less or no cold drinks or food even after the administration period.

In another embodiment, the patient reduces the consumption of spices (including but not limited to peppers and garlic) to a minimum, preferably eliminating spices from his diet, for the administration period. A limited consumption of spices may be acceptable during the administration period. Frequent consumption of spices may offset the effectiveness of certain herbs in the composition. Preferably, the patient alters his/her lifestyle to consume less or no spices even after the administration period.

In another embodiment, the patient reduces the consumption of raw foods to a minimum for the administration period. Raw food includes but is not limited to raw vegetables, raw fish, raw meat, and raw fruits). Preferably, the patient alters his/her lifestyle to consume less or no raw food even after the administration period.

In another embodiment, the patient reduces the frequency of sexual intercourse, preferably eliminating intercourse, for the administration period. Frequent sexual stimulation may inflate the prostate.

In another embodiment, the patient reduces emotional stress, attempting to keep emotional stress to a minimum for the administration period. Emotional disturbances may cause various health related problems leading to reduced viability of the treatment.

In another embodiment, the patient substantially abstains from consumption of cold drinks, cold food, spices, and raw food, reduces the frequency of sexual intercourse and reduces emotional stress during the administration period.

EXAMPLE 1

The following ingredients were combined in a capsule. The about 40 to about 45 grams capsules were taken two to three times a day for about 180 to about 730 days with no side effects.

The effective rate of this study was about 100%. Two of the patients tested for prostate cancer by biopsy before treatment by the following capsule. After treatment, these patients had no prostate cancer as determined by a biopsy. All of the patients had normal PSA after an administration period with no side-effects reported.

All percentages given in this application are weight percentages, unless otherwise specified.

| Chinese Name (Pin Yin) | Latin | Percentage (by weight) |
|---|---|---|
| Huang Qi (Sheng) | Astragali seu Hedysari Radix | 5.7 |
| Dang Shen | Codonopsis Pilosulae Radix | 5.7 |
| Bai Zhu | Atractylodes Rhizoma | 8.5 |
| Fu Ling | Poria Cocos | 11.4 |
| Lai Fu Zi | Raphani Semen | 5.2 |
| Gan Jiang | Zingiberis Siccatum Rhizoma | 5.7 |
| Sheng Di Huang | Rehmanniae Radix | 5.7 |
| Zhi Zi | Gardeniae Fructus | 5.7 |
| Mu Dan Pi | Moutan Radicis Cortx | 5.7 |
| Jin Qian Cao | Glechoma Herba | 5.7 |
| Bei Xie | Dioscoreae Hypoglauca Rhizoma | 5.7 |
| Hai Jin Sha | Lygodii Spora | 3.7 |
| Mu Li (Duan) | Ostreae Testa | 5.7 |
| Niu Xi (Huai) | Achyranthis Radix | 5.7 |
| Ba Ji Tian | Morin dae Radix | 5.7 |
| Shou Di Huang | Rehmanniae Radix | 8.5 |

It is to be understood that while the invention has been described in conjunction with the detailed description thereof, that the foregoing description is intended to illustrate and not limit the scope of the invention, which is defined by the scope of the appended claims. Other aspects, advantages, and modifications are evident from a review of the following claims.

What is claimed is:

1. A composition comprising Astragali seu hedysari radix, Codonposis pilosulae radix, Atractylodes rhizoma, Poria cocos, Raphani semen, Zingiberis siccatun rhizoma, Rehmanniae radix, Gardeniae fructus, Moutan radicis cortex, Glechoma herba, Dioscoreae hypoglauca rhizoma, Lygodii spora, Ostrea tests, Achyranthis radix, Morindae radix, and Rehmanniae radix.

2. The composition of claim 1 wherein the percentages of the total composition are:
   5.7% astragali seu hedysari radix,
   5.7% Codonopsis pilosulse radix,
   8.5% Atractylodes rhizoma,
   11.4% Poria cocos,
   5.2% Raphani semen,
   5.7% Zingiberis siccatun rhizoms,
   5.7% Rehmanniae radix,
   5.7% Gardeniae fructus,
   5.7% Moutan radicis cortex,
   5.7% Glechoma herbs, 5.7% Dioscoreae hypoglauca rhizoma,
3.7% Lygodii spora,
5.7% Ostreae testa,
5.7% Achyranthis radix,
5.7% Morindae radix, and
8.5% Rehmanniae radix.

3. The composition of claim 1 wherein the composition is prepared as a tea.

4. The composition of claim 1 wherein the composition is in a capsule.

5. The composition of claim 1 wherein the composition is a powder.

6. The composition of claim 1 wherein the composition is an extract obtained by using a chemical solvent.

* * * * *